(12) United States Patent
Hwang

(10) Patent No.: US 11,376,042 B2
(45) Date of Patent: Jul. 5, 2022

(54) SECTION-GUIDE GRADUATED RULER FOR CAESAREAN SECTION

(71) Applicant: Tae Woong Hwang, Busan (KR)

(72) Inventor: Tae Woong Hwang, Busan (KR)

( * ) Notice: Subject to any disclaimer, the term of this patent is extended or adjusted under 35 U.S.C. 154(b) by 394 days.

(21) Appl. No.: 16/618,627

(22) PCT Filed: Oct. 31, 2018

(86) PCT No.: PCT/KR2018/013065
§ 371 (c)(1),
(2) Date: Dec. 2, 2019

(87) PCT Pub. No.: WO2019/107760
PCT Pub. Date: Jun. 6, 2019

(65) Prior Publication Data
US 2020/0187972 A1    Jun. 18, 2020

(30) Foreign Application Priority Data
Nov. 29, 2017   (KR) .......................... 10-2017-0161631

(51) Int. Cl.
*A61B 17/42*   (2006.01)
*A61B 90/00*   (2016.01)
*A61B 17/3211*   (2006.01)

(52) U.S. Cl.
CPC .............. *A61B 17/42* (2013.01); *A61B 90/06* (2016.02); *A61B 17/3211* (2013.01); *A61B 2090/061* (2016.02)

(58) Field of Classification Search
CPC ... A61B 17/42; A61B 90/06; A61B 2090/061; A61B 2017/320052; A61B 5/43; A61B 5/4306; A61B 5/4319; A61B 5/425; A61B 5/4337; A61B 5/4343; G01B 3/02; G01B 3/10; G01B 3/1089; B43L 7/00; B43L 7/02; B43L 13/20; B43L 13/142
See application file for complete search history.

(56) References Cited

U.S. PATENT DOCUMENTS

| | | | |
|---|---|---|---|
| 2013/0304080 A1* | 11/2013 | Landry | A61B 17/42 606/121 |
| 2013/0325046 A1* | 12/2013 | Terwiske | A61B 17/32 606/167 |
| 2016/0270695 A1* | 9/2016 | Trokel | A61B 5/1072 |

FOREIGN PATENT DOCUMENTS

| | | | |
|---|---|---|---|
| CN | 206007376 U | * | 3/2017 |
| JP | 2010-075318 A | | 4/2010 |
| KR | 20-1997-0004669 U | | 2/1997 |
| KR | 20-0433852 Y1 | | 12/2006 |

(Continued)

OTHER PUBLICATIONS

International Search Report dated Feb. 1, 2019, issued to International Application No. PCT/KR2018/013065.

*Primary Examiner* — Katherine H Schwiker
*Assistant Examiner* — Serenity A Miller
(74) *Attorney, Agent, or Firm* — Stein IP, LLC

(57) ABSTRACT

The section-guide graduated ruler for Caesarean section according to the present subject matter includes: a strip-shaped vertical tape having pointed upper and lower ends and having a length corresponding to the distance from the mother's navel to clitoris, and a horizontal tape coupled so as to intersect with the vertical tape, the horizontal tape having a length corresponding to the length of both ilia, thereby guiding a Pfannenstiel incision during Caesarean section.

7 Claims, 4 Drawing Sheets

(56) References Cited

FOREIGN PATENT DOCUMENTS

| KR | 10-2012-0026772 A | 3/2012 |
|---|---|---|
| KR | 10-1896198 B1 | 9/2018 |

* cited by examiner

[FIG. 1]
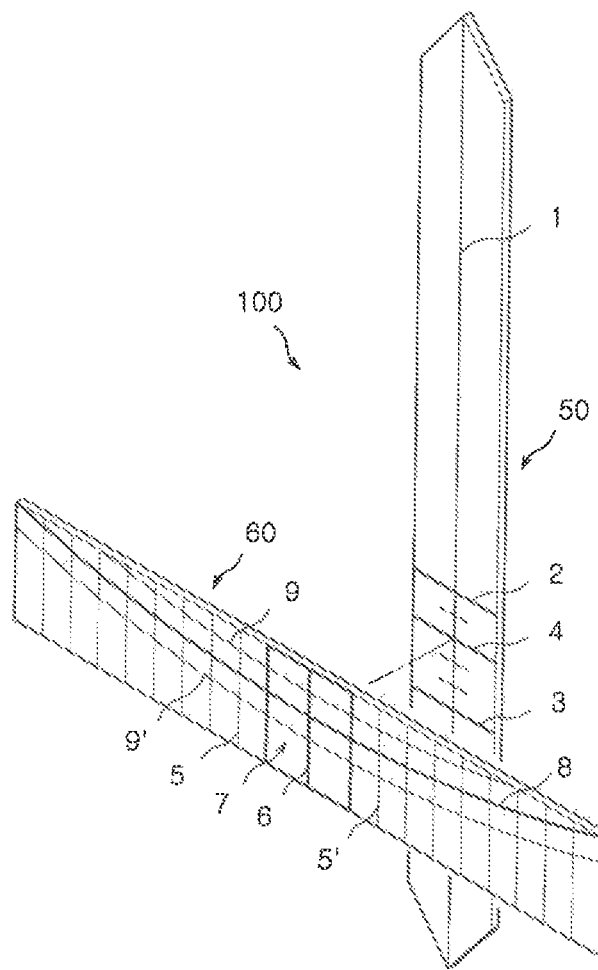

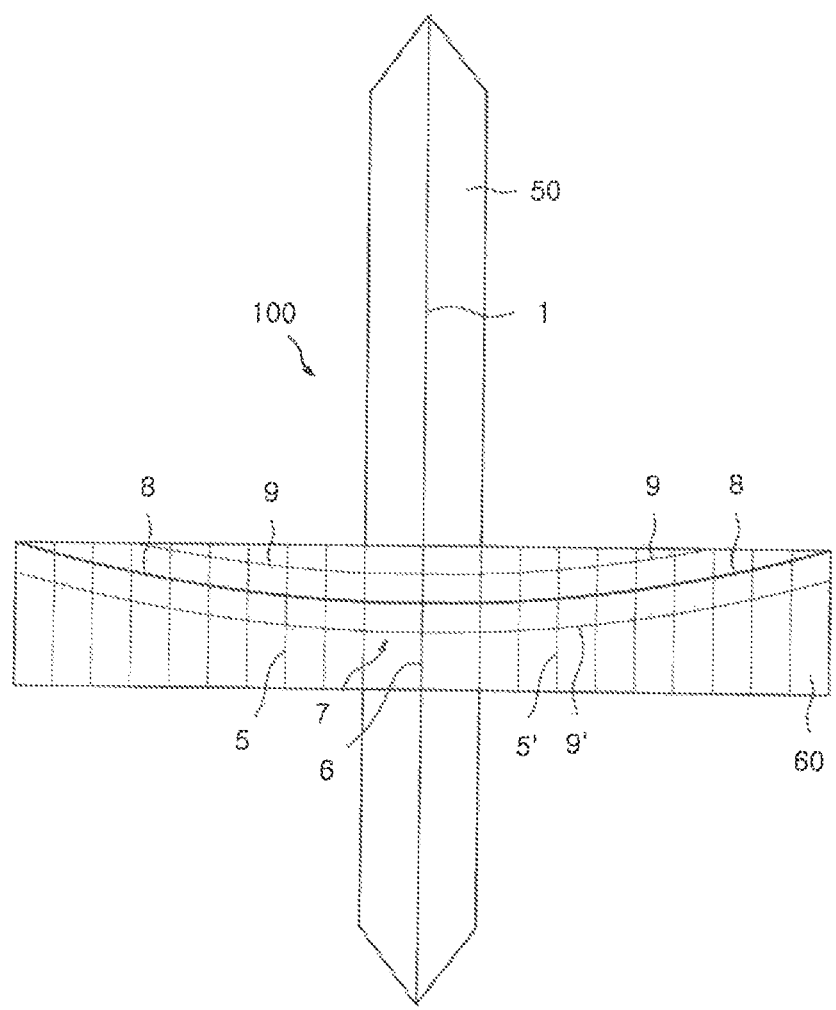
[FIG. 2]

[FIG. 3]
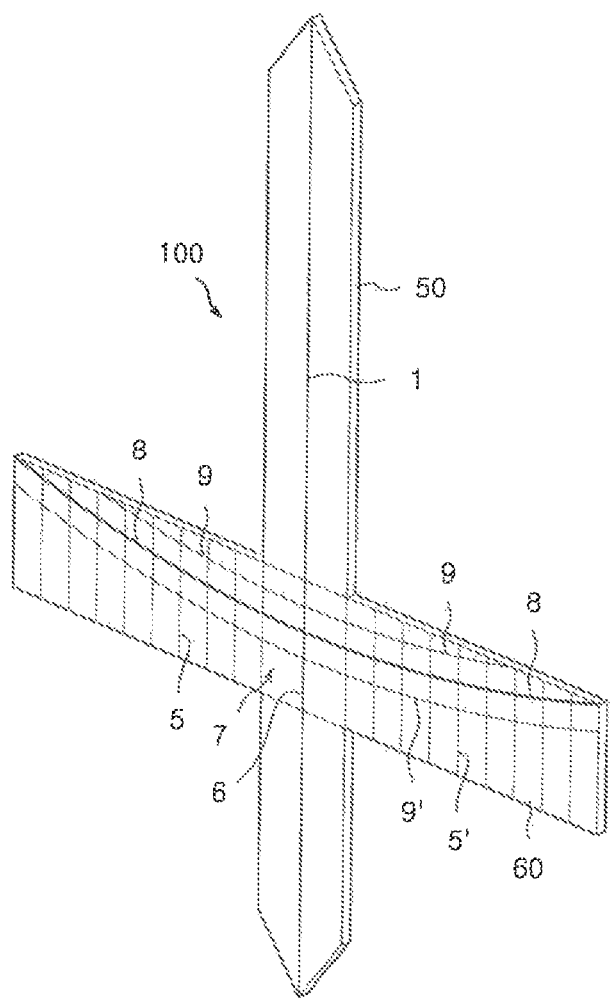

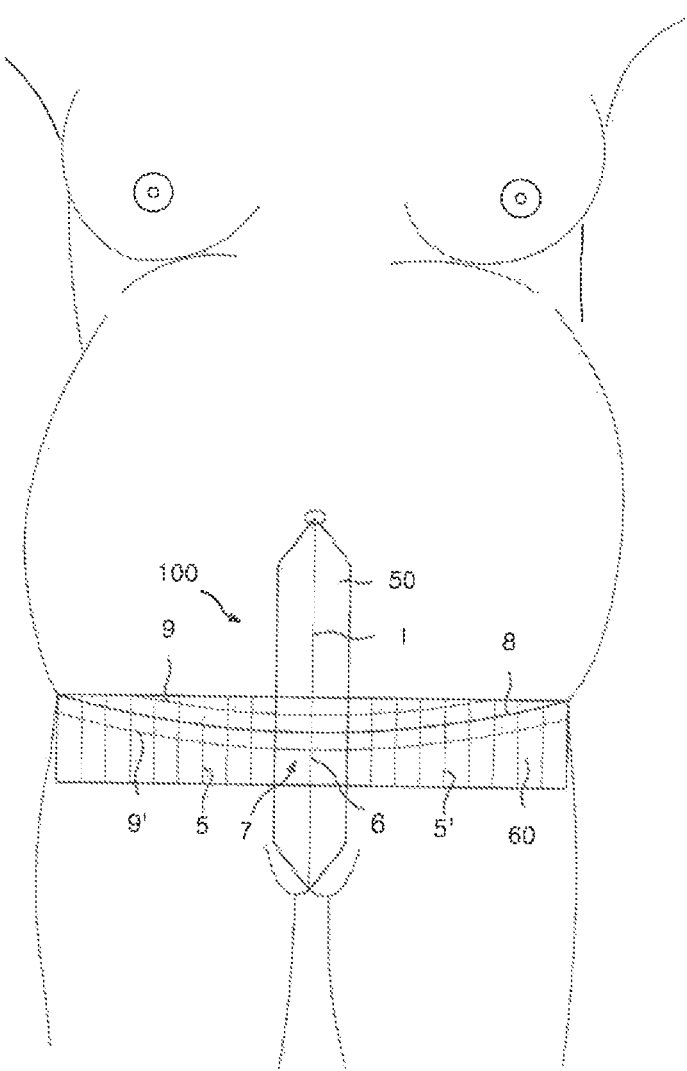
[FIG. 4]

SECTION-GUIDE GRADUATED RULER FOR CAESAREAN SECTION

CROSS-REFERENCE TO RELATED APPLICATIONS

This application is a national stage of International Application No. PCT/KR2018/013065, filed Oct. 31, 2018, which claims the benefit of Korean Application No. 10-2017-0161631, filed Nov. 29, 2017, in the Korean Intellectual Property Office, the disclosures of which are incorporated herein by reference.

TECHNICAL FIELD

The present invention relates to a section-guide graduated ruler for a Caesarean section. More particularly, the present invention relates to a section-guide graduated ruler for a Caesarean section wherein, when natural delivery of a baby in the mother's womb through the birth canal is deemed difficult, and when Caesarean section surgery is accordingly performed in which a small incision line is drawn across the mother's abdomen and womb to deliver the baby through a surgical procedure, the graduated ruler guides a Pfannenstiel incision so as to have vertical and lateral symmetry such that an accurate incision location is guided not only for an experienced surgeon but also for a beginner, thereby forming a clean surgical scar.

BACKGROUND ART

In the old days when medicine was not developed, the birth of pregnant women was only carried out naturally. However, there are many cases where both the mother and a baby are in a dangerous state during natural delivery. In recent years, due to the development of medicine, various delivery methods such as painless delivery and water birth have been attempted to alleviate the pain that a pregnant woman may experience during natural delivery. When the mother's pelvis is narrow or there is late childbirth or the mother has pregnancy toxemia or other diseases including placenta previa and thus natural delivery of a baby is deemed impossible, the child is delivered by Caesarean delivery, in which an incision is made in the mother's abdomen and womb and the child is pulled out for the health of the mother and child.

In addition, recently people are marrying later, and there are many incidences of an older couple having a late child and thus, late childbirth is increasing, and there are many pregnant women who give birth by a Caesarean section because of fear of pain of childbirth even when natural birth is possible.

When undergoing such a Caesarean section, a woman does not suffer from childbirth, while under general anesthesia, an incision is made in a woman's abdomen and womb with a scalpel, which entails the risk of surgery and a surgical site that is cut remains scarred after childbirth for women who are interested in beauty treatments.

In general, examples of the Caesarean section include a midline vertical incision vertically along the midline of the abdomen from below the mother's navel to the pubis, and a Pfannenstiel incision in which the mother's lower abdomen is cut slightly above the mother's pubis using a crescent-shaped transverse curve. The former has a merit in that it takes less time to operate and there is a wider field of view thereby making it easier to operate, but has a disadvantage in that the scar is formed vertically and thus is not aesthetically pleasing to the eye. The Pfannenstiel incision takes a long time, but there is an advantage that the scar is formed on the upper portion of the pubis and covered with underwear. Therefore, in recent years, surgery is performed mainly using the latter Pfannenstiel incision.

However, with regards to the Pfannenstiel incision, there is a difficulty in forming the incision line at the correct location for easy delivery and correctly forming the semi-circle symmetrically with respect to the navel. Therefore, for inexperienced beginners, including inexperienced surgeons, it is not easy to set up the incision location, and even the skilled person estimates the incision location and makes incisions so that the incision line is not symmetrical and crooked and thus the incision scar after surgery is unsightly.

DISCLOSURE

Technical Problem

The present invention is directed to providing a section-guide graduated ruler for a Caesarean section wherein, during the Caesarean section by a Pfannenstiel incision, an incision line is drawn so as to have vertical and lateral symmetry and the accurate incision location is guided.

The present invention is also directed to providing a section-guide graduated ruler for a Caesarean section wherein a semi-circular incision line is guided so that the incision line is not crooked during a Caesarean section.

Technical Solution

One aspect of the present invention provides a section-guide graduated ruler for a Caesarean section including a strip-shaped vertical tape having pointed upper and lower ends and having a length corresponding to the distance from the mother's navel to clitoris, and a horizontal tape coupled so as to intersect with the vertical tape, the horizontal tape having a length corresponding to the length of both ilia, thereby guiding a Pfannenstiel incision during the Caesarean section.

A dividing line may be indicated in a middle of the vertical tape so as to divide the vertical tape into two parts in a lengthwise direction, and each of a horizontal line and a pubic coupling line with which top and bottom surfaces of the horizontal tape coincide may be indicated at a lower portion of the middle of the vertical tape so as to intersect with the dividing line, and an incision line may be indicated between the horizontal line and the pubic coupling line horizontally or in an arced shape.

Vertical scales may be indicated on the horizontal tape spaced apart at a certain distance, and a rectangular contour line including a vertical line that coincides with a dividing line of the vertical tape may be indicated in a middle of the horizontal tape that overlaps the vertical tape, and an incision baseline that coincides with an incision line of the vertical tape while intersecting with the rectangular contour line may be indicated at edges of both top ends of the horizontal tape and have an arced shape.

The vertical tape and the horizontal tape may be formed as one body in a cross shape, thereby forming a dividing line on the vertical tape, and an arced incision baseline that connects edges of both ends of the horizontal tape may be indicated on the horizontal tape.

Auxiliary incision lines may be indicated on upper and lower portions of the incision baseline.

A length of the vertical tape may be in the range from 30 to 35 cm, and a width of the vertical tape may be about 4 cm so that the vertical tape may be within 2 cm laterally with respect to the dividing line, and a width from the pubic coupling line that coincides with the pubis to the horizontal line may be 5 cm, and the incision line may be formed at a location of 3 cm from the pubic coupling line.

The horizontal tape may have a length ranging from 32 to 38 cm in consideration of a length to both ilia, and a width of the horizontal tape may be 5 cm which is the same as a length from a horizontal line to a pubic coupling line of the vertical tape, and the incision baseline that intersects with the middle rectangular contour line may be indicated in a gradually curved arced shape so that an intersecting point thereof is formed at a location of 3 cm from the bottom.

Advantageous Effects

According to the present invention, the incision location having vertical and lateral symmetry can be guided by simply attaching a section-guide graduated ruler for a Caesarean section to the mother's abdomen during the Caesarean section by a Pfannenstiel incision so that the accurate incision location can be provided regardless of skillfulness of a surgeon and thus a clean and correct scar can be formed after surgery and thus this is effective for helping women with beauty treatments.

DESCRIPTION OF DRAWINGS

FIG. 1 is an exploded perspective view of a graduated ruler according to an embodiment of the present invention.

FIG. 2 is an exemplary view illustrating a state in which the graduated ruler of FIG. 1 is coupled.

FIG. 3 is a perspective view of a graduated ruler according to another embodiment of the present invention.

FIG. 4 is an exemplary view illustrating the usage of the present invention.

BEST MODE OF THE INVENTION

Hereinafter, a best mode for implementing the present invention will be described in detail with reference to the accompanying drawings.

As shown in FIGS. 1 and 2, a graduated ruler 100 according to the present invention includes a strip-shaped vertical tape 50 having pointed upper and lower ends and having a length corresponding to the distance from the mother's navel to clitoris, and a horizontal tape 60 coupled so as to intersect with the vertical tape 50, the horizontal tape having a length corresponding to the length of both ilia.

A dividing line 1 in the middle of the vertical tape 50 is indicated on the vertical tape 50 so as to divide the vertical tape 50 into two parts in a lengthwise direction, and each of a horizontal line 2 and a pubic coupling line 3 with which top and bottom surfaces of the horizontal tape 60 coincide, is indicated at the lower portion of the middle of the vertical tape 50 so as to intersect with the dividing line 1, and an incision line 4 is indicated between the horizontal line 2 and the pubic coupling line 3 horizontally or in an arced shape.

Vertical scales 5 and 5' are indicated on the horizontal tape 60 at a certain distance, and a rectangular contour line 7 including a vertical line 6 that coincides with the dividing line 1 of the vertical tape 50 is indicated in the middle that overlaps the vertical tape 50, and an incision baseline 8 that coincides with the incision line 4 of the vertical tape 50 while intersecting with the rectangular contour line 7 is indicated at edges of both top ends of the horizontal tape 60 to have an arced shape.

In addition, auxiliary incision lines 9 and 9' are indicated on upper and lower portions of the incision baseline 8 at a certain distance.

In another embodiment of the present invention, the vertical tape 50 and the horizontal tape 60 are separated from each other, not coupled to each other, and intersect with each other so as to be formed as one body in a cross shape, as shown in FIG. 3, thereby forming the dividing line 1 on the vertical tape 50, and the arced incision baseline 8 for connecting edges of both ends of the horizontal tape 60 may be indicated on the horizontal tape 60, and as in the embodiment described above, the vertical line 6, the incision line 4, and the pubic coupling line 3 are not indicated on the vertical tape 50.

In the graduated ruler 100 according to the embodiment of the present invention described above, the length of the vertical tape 50 is slightly different according to the mother's body shape but, preferably, may be in the range from 30 to 35 cm, and the width of the vertical tape 50 may be about 4 cm and thus may be within 2 cm laterally with respect to the dividing line 1, and the width from the pubic coupling line 3 that coincides with the pubis to the horizontal line 2 may be 5 cm, wherein the incision line 4 is formed at a location 3 cm from the pubic coupling line 3.

Also, the horizontal tape 60 may have a length ranging from 32 to 38 cm in consideration of the length to both ilia, and the width of the horizontal tape 60 may be 5 cm, which is the same as the length from the horizontal line 2 to the pubic coupling line 3 of the vertical tape 50, wherein the incision baseline 8 that intersects with the middle rectangular contour line 7 is indicated in a gradually curved arced shape so that the intersecting point thereof may be formed at the location of 3 cm from the bottom.

In this way, the vertical tape 50 and the horizontal tape 60 according to the present invention are made of a transparent and soft material, and an adhesive is applied to back surfaces of the vertical tape 50 and the horizontal tape 60 so that the vertical tape 50 and the horizontal tape 60 are easily attachable to or detachable from the mother's abdomen. During incision of the abdomen for a Caesarean section, first, the vertical tape 50 is adjusted to the clitoris from the navel and thus is vertically attached. In this case, the mother's pubis is found by a surgeon's hand, and the vertical tape 50 and the horizontal tape 60 are attached to the mothers pubis so that the pubic coupling line 3 is located at the mother's pubis. Then, both sides of a top end of the horizontal tape 60 are adjusted to the mother's both ilia and intersect with the top surface of the vertical tape 50 so that the bottom coincides with the pubic coupling line 3 of the horizontal tape 60. Thus, the vertical tape 50 and the horizontal tape 60 are attached to the mother's abdomen in a cross shape as shown in FIG. 2.

Because of the structure of the body, the incision line 4 for the mother's Cesarean section incision is 3 cm above the pubis so that the intersection point of the incision baseline 8 of the horizontal tape 60 that intersects with the dividing line 1 of the vertical tape 50 coincides with 3 cm above the pubic coupling line 3. Thus, the incision baseline 8 is the incision line 4 for cutting the mother's abdomen.

Since the incision baseline 8 has an arc shape connected to both upper ends of the horizontal tape 60 around the intersection point with the dividing line 1 of the vertical tape 50, a gradually curved guide line for Pfannenstiel incision is visually provided to the surgeon.

Accordingly, the surgeon cuts a necessary length according to an incision criterion indicated by the semi-circular arc shape. The incision length is formed by cutting laterally along the incision baseline 8 with respect to the vertical line 6 that is vertically indicated on the rectangular contour line 7 of the horizontal tape 60. In this case, when the incision is made in a certain length so that the left and right are the same by using the vertical scales 5 and 5' indicated on the outside of the rectangular contour line 7 at a certain distance, the mother's abdomen is correctly cut to a certain length laterally along the arc-shaped incision baseline 8.

In general, when a Caesarean section, i.e., a Pfannenstiel Incision, is made, the semi-circular incision line 4 is slightly different for each surgeon and the shape of the incisions line 4 is determined according to skillfulness. Thus, a surgical scar is formed differently for each mother. According to the present invention, since the section-guide graduated ruler for a Caesarean section is simply attached to the mother's abdomen during surgery and guides the certain incision line 4, the problem that the length is not constant and the incision line is crooked is solved.

Here, because the auxiliary incision lines 9 and 9' are indicated on the upper and lower portions of the incision baseline 8, it is also possible to make an incision using the upper and lower auxiliary incision lines 9 and 9' without using the incision baseline 8 according to the difference in the location of the mother's womb or the surgical method of the surgeon.

In addition, according to the present invention, the horizontal tape 60 and the vertical tape 50 are separated from each other, not coupled to each other, and are formed as a one body in a cross shape, as shown in FIG. 3. Thus, when, as in the embodiment described above, the dividing line 1 is formed on the vertical tape 50, and the arc-shaped incision baseline 8 for connecting edges of both upper ends of the horizontal tape 60 is indicated on the horizontal tape 60, the incision line 4 is conveniently guidable by one attachment to the mother's abdomen during surgery.

As such, according to the present invention, the section-guide graduated ruler for a Caesarean section is simply attached to the mother's abdomen during the Caesarean section so that the semi-circular incision line 4 is guidable so as to have vertical and lateral symmetry. Thus, the surgical location can be accurately known, the incision line 4 is not crooked and correctly formed, a clean surgical scar is formed, and this helps women with beauty treatments.

The invention claimed is:

1. A section-guide graduated ruler for a Caesarean section, comprising:
    a strip-shaped vertical tape (50) having pointed upper and lower ends and having a length corresponding to a distance from a mother's navel to clitoris; and
    a horizontal tape (60) coupled so as to intersect with the vertical tape (50), the horizontal tape (60) having a length corresponding to a length of both ilia, thereby guiding a Pfannenstiel incision during the Caesarean section,
    wherein vertical scales (5)(5') are indicated on the horizontal tape (60) spaced apart at a certain distance, and a rectangular contour line (7) including a vertical line (6) that coincides with a dividing line (1) of the vertical tape (50) is indicated in a middle of the horizontal tape (60) that overlaps the vertical tape (50), and an incision baseline (8) that coincides with an incision line (4) of the vertical tape (50) while intersecting with the rectangular contour line (7) is indicated at top corners of the horizontal tape (60) and has an arced shape.

2. The section-guide graduated ruler of claim 1, wherein auxiliary incision lines (9)(9') are indicated above and below the incision baseline (8).

3. The section-guide graduated ruler of claim 1, wherein the length of the vertical tape (50) is in a range from 30 to 35 cm, and a width of the vertical tape (50) is about 4 cm so that the vertical tape (50) is within 2 cm laterally with respect to the dividing line (1), and a width from a pubic coupling line (3) that is configured to coincide with the pubis to a horizontal line (2) is 5 cm, and the incision line (4) is formed at a location of 3 cm from the pubic coupling line (3).

4. The section-guide graduated ruler of claim 1, wherein the length of the horizontal tape (60) ranges from 32 to 38 cm corresponding to the length of both ilia, and a width of the horizontal tape (60) is 5 cm which is the same as a length from a horizontal line (2) to a pubic coupling line (3) of the vertical tape (50), and the incision baseline (8) that intersects with the middle rectangular contour line (7) is indicated in a gradually curved arced shape so that an intersecting point thereof is formed.

5. A section-guide graduated ruler for a Caesarean section, comprising:
    a strip-shaped vertical tape (50) having pointed upper and lower ends and having a length corresponding to a distance from a mother's navel to clitoris; and
    a horizontal tape (60) coupled so as to intersect with the vertical tape (50), the horizontal tape (60) having a length corresponding to a length of both ilia, thereby guiding a Pfannenstiel incision during the Caesarean section,
    wherein the vertical tape (50) and the horizontal tape (60) are formed as one body in a cross shape, thereby forming a dividing line (1) on the vertical tape (50), and an arced incision baseline (8) that connects edges of both ends of the horizontal tape (60) is indicated on the horizontal tape (60).

6. The section-guide graduated ruler of claim 5, wherein auxiliary incision lines (9)(9') are indicated above and below the incision baseline (8).

7. A section-guide graduated ruler for a Caesarean section, comprising:
    a strip-shaped vertical tape (50) having pointed upper and lower ends and having a length corresponding to a distance from a mother's navel to clitoris; and
    a horizontal tape (60) coupled so as to intersect with the vertical tape (50), the horizontal tape (60) having a length corresponding to a length of both ilia, thereby guiding a Pfannenstiel incision during the Caesarean section,
    wherein the length of the horizontal tape (60) ranges from 32 to 38 cm corresponding to the length of both ilia, and a width of the horizontal tape (60) is 5 cm which is the same as a length from a horizontal line (2) to a pubic coupling line (3) of the vertical tape (50), and an incision baseline (8) that intersects with a middle rectangular contour line (7) is indicated in a gradually curved arced shape so that an intersecting point thereof is formed.

* * * * *